United States Patent
Nakanishi

(10) Patent No.: US 9,439,626 B2
(45) Date of Patent: Sep. 13, 2016

(54) ATTACHMENT FOR ULTRASONIC PROBE, ULTRASONIC PROBE, ELECTRONIC DEVICE, AND ULTRASONIC DIAGNOSTIC APPARATUS

(71) Applicant: SEIKO EPSON CORPORATION, Tokyo (JP)

(72) Inventor: Daisuke Nakanishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 94 days.

(21) Appl. No.: 14/015,043

(22) Filed: Aug. 30, 2013

(65) Prior Publication Data

US 2014/0066779 A1    Mar. 6, 2014

(30) Foreign Application Priority Data

Sep. 3, 2012  (JP) ................. 2012-192861

(51) Int. Cl.
*A61B 8/00* (2006.01)
*B06B 3/00* (2006.01)
*B06B 1/06* (2006.01)

(52) U.S. Cl.
CPC ........... *A61B 8/4444* (2013.01); *A61B 8/4483* (2013.01); *A61B 8/587* (2013.01); *B06B 3/00* (2013.01); *A61B 8/4405* (2013.01); *A61B 8/4411* (2013.01); *A61B 8/4427* (2013.01); *B06B 1/0629* (2013.01)

(58) Field of Classification Search
CPC ........... A61B 8/14; A61B 8/13; A61B 8/00; A61B 8/4444; A61B 8/4427; A61B 8/4405; A61B 8/4483; A61B 8/587; A61B 8/4411; A61N 7/00; B06B 3/00; B06B 1/0629
USPC ....................................................... 600/459
See application file for complete search history.

(56) References Cited

U.S. PATENT DOCUMENTS

| | | | |
|---|---|---|---|
| 5,348,013 A | 9/1994 | Kanda et al. | |
| 5,507,293 A | 4/1996 | Tannaka et al. | |
| 2002/0068871 A1* | 6/2002 | Mendlein et al. | ............ 600/459 |
| 2004/0060340 A1* | 4/2004 | Hibi | ............... G09B 23/286 73/1.86 |
| 2004/0260181 A1 | 12/2004 | Makita et al. | |
| 2010/0017163 A1* | 1/2010 | Yamaguchi | ............... G01J 5/02 702/99 |
| 2010/0049050 A1* | 2/2010 | Pelissier | .................. A61B 8/00 600/443 |
| 2010/0142315 A1* | 6/2010 | Nassiri et al. | .................. 367/13 |
| 2011/0009734 A1* | 1/2011 | Foley | ....................... A61N 7/02 600/411 |
| 2012/0071758 A1* | 3/2012 | Lachaine | ............... A61B 8/085 600/439 |
| 2013/0150722 A1 | 6/2013 | Kiyose et al. | |

FOREIGN PATENT DOCUMENTS

| | | |
|---|---|---|
| JP | 05-042138 A | 2/1993 |
| JP | 06-090954 A | 4/1994 |
| JP | 07-155321 A | 6/1995 |
| JP | 07-289554 A | 11/1995 |
| JP | 2000-139905 A | 5/2000 |
| JP | 2004-230033 A | 8/2004 |
| JP | 2006-204617 A | 8/2006 |
| JP | 2007-142555 A | 6/2007 |
| JP | 2008-259541 A | 10/2008 |
| JP | 2010-119481 A | 6/2010 |
| JP | 2013-123459 A | 6/2013 |

* cited by examiner

*Primary Examiner* — Tse Chen
*Assistant Examiner* — Charles G Chiang
(74) *Attorney, Agent, or Firm* — Global IP Counselors, LLP

(57) ABSTRACT

An attachment for an ultrasonic probe is adapted to be mounted onto an ultrasonic probe body of the ultrasonic probe. The attachment for an ultrasonic probe includes a cover member and a protective member. The cover member is configured and arranged to cover an ultrasonic wave emission surface of a head section of the ultrasonic probe body when the attachment is mounted onto the ultrasonic probe body. The protective member is provided to a surface of the cover member facing the ultrasonic wave emission surface, and configured and arranged to be in contact with the ultrasonic wave emission surface when the attachment is mounted onto the ultrasonic probe body.

18 Claims, 14 Drawing Sheets

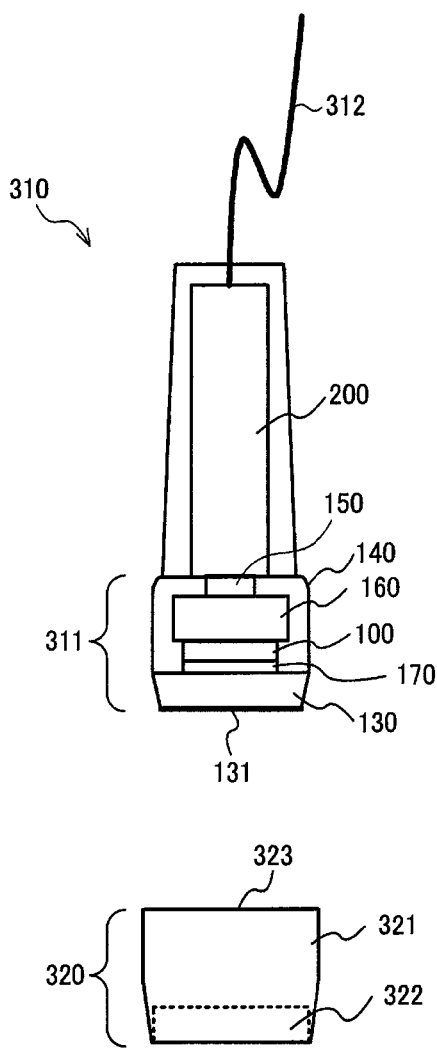
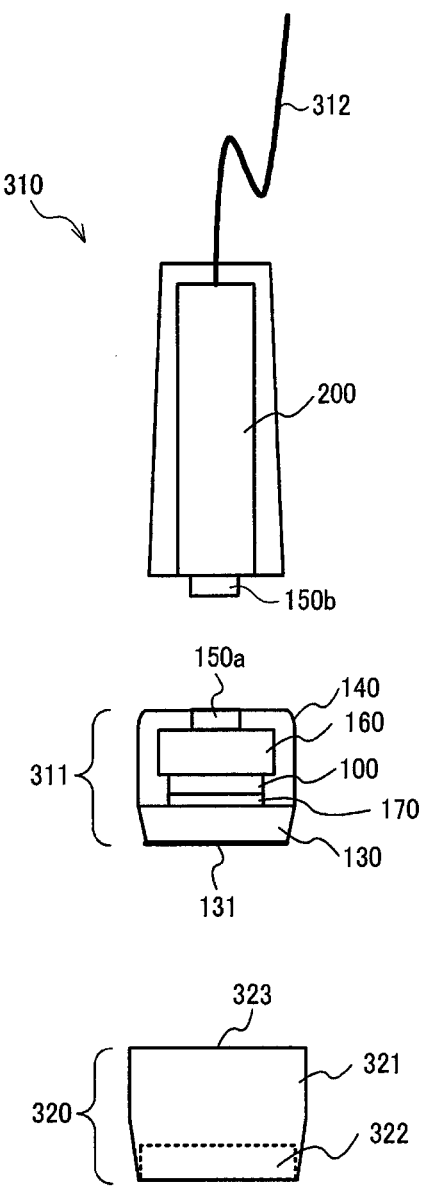
Fig. 4A
Fig. 4B
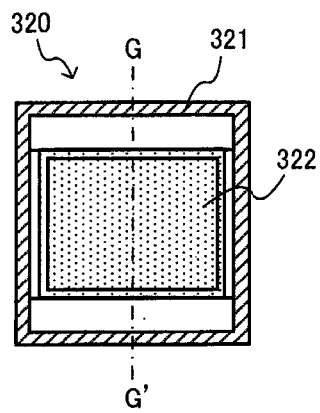
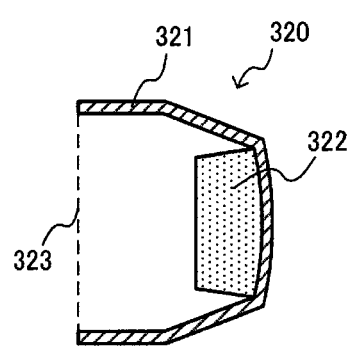
Fig. 4C    Fig. 4D

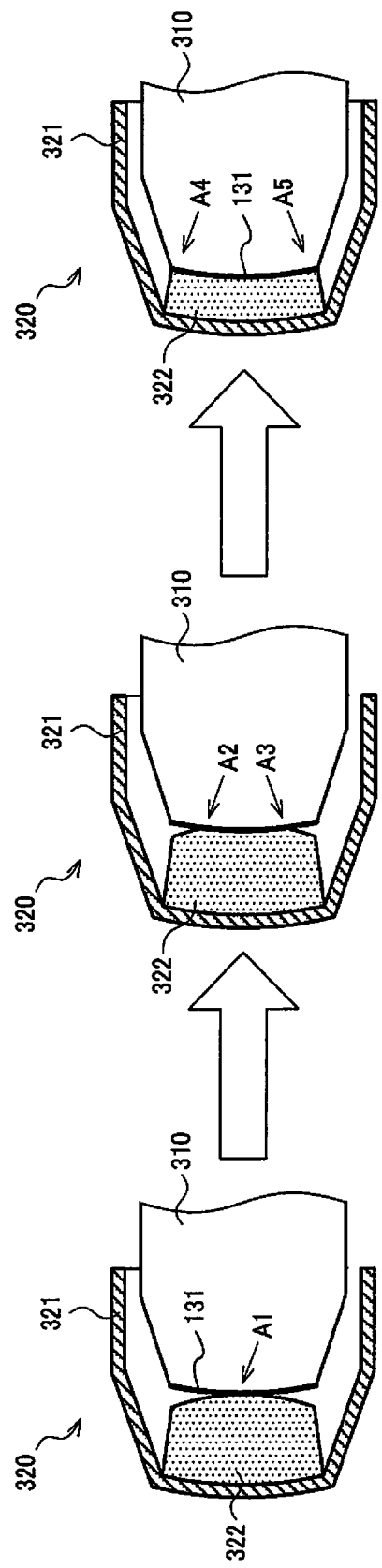

ATTACHMENT FOR ULTRASONIC PROBE, ULTRASONIC PROBE, ELECTRONIC DEVICE, AND ULTRASONIC DIAGNOSTIC APPARATUS

CROSS-REFERENCE TO RELATED APPLICATIONS

This application claims priority to Japanese Patent Application No. 2012-192861 filed on Sep. 3, 2012. The entire disclosure of Japanese Patent Application No. 2012-192861 is hereby incorporated herein by reference.

BACKGROUND

1. Technical Field

The present invention relates to an attachment for an ultrasonic probe, an ultrasonic probe, an electronic device, an ultrasonic diagnostic apparatus, and the like.

2. Related Art

A known example of a device for emitting ultrasonic waves toward an object and receiving reflected waves coming from interfaces of different acoustic impedance in the interior of the object is an ultrasonic diagnostic apparatus for examining the interior of a human body.

As an ultrasonic probe to be used in an ultrasonic diagnostic apparatus, for example, Japanese Laid-Open Patent Application Publication 2007-142555 discloses a feature in which piezoelectric elements are arrayed in a matrix array and caused to emit ultrasonic beams. Expected examples of applying ultrasonic diagnostic apparatuses include expansion into health care fields in which image diagnosis of a surface layer of a subject is used, such as measuring the visceral fat and measuring the blood flow rate. Such applications also include a considerable need for miniaturized, portable ultrasonic diagnostic apparatuses.

SUMMARY

However, portable diagnostic apparatuses and the like are susceptible to damage to an ultrasonic element such as through a user accidentally causing an impact against the ultrasonic probe when carrying the apparatus. Additionally, a process for adjusting the ultrasonic probe necessitates, for example, an ultrasonic phantom, but it is inconvenient for the user to have to carry the ultrasonic phantom along with the portable diagnostic apparatus.

According to several aspects of the present invention, it is possible to provide an attachment for an ultrasonic probe, an ultrasonic probe, an electronic device, an ultrasonic diagnostic apparatus, and the like making it possible to readily carry out a process for adjusting an ultrasonic probe by a simple configuration.

One aspect of the present invention relates to an attachment for an ultrasonic probe that is adapted to be mounted onto an ultrasonic probe body of the ultrasonic probe. The attachment for an ultrasonic probe includes a cover member and a protective member. The cover member is configured and arranged to cover an ultrasonic wave emission surface of a head section of the ultrasonic probe body when the attachment is mounted onto the ultrasonic probe body. The protective member is provided to a surface of the cover member facing the ultrasonic wave emission surface, and configured and arranged to be in contact with the ultrasonic wave emission surface when the attachment is mounted onto the ultrasonic probe body.

According to the one aspect of the present invention, mounting the attachment for an ultrasonic probe makes it possible to protect the ultrasonic probe body, and thus makes it possible to prevent damage to the ultrasonic probe. An adjustment process for the ultrasonic probe body can also be carried out using either the protective member or the protective member and the cover member as an ultrasonic phantom when the attachment for an ultrasonic probe has been attached, and thus the need to have already separately prepared an ultrasonic phantom for the adjustment process can be obviated, and the adjustment process can be readily carried out with a simple configuration.

In the one aspect of the present invention, the protective member is preferably formed of a shape and material configured and arranged to be in intimate contact with the ultrasonic wave emission surface when the attachment is mounted onto the ultrasonic probe body.

In so doing, the protective member and the ultrasonic wave emission surface can be brought into intimate contact with each other and air or the like can be prevented from entering in a gap between the two, and thus a higher-precision adjustment process can be carried out.

In the one aspect of the present invention, a surface of the protective member that faces the ultrasonic wave emission surface preferably has a convex shape before the attachment is mounted onto the ultrasonic probe body.

In so doing, when the attachment for an ultrasonic probe is being mounted, first there can be contact between the convex section of the protective member and the ultrasonic wave emission surface, thus pushing air out to the outside. As a result, the protective member and the ultrasonic wave emission surface can be placed in intimate contact with each other.

In the one aspect of the present invention, a surface of the protective member that faces the ultrasonic wave emission surface preferably has an inclined shape before the attachment is mounted onto the ultrasonic probe body.

In so doing, when the attachment for an ultrasonic probe is being mounted, first one end of the protective member and the ultrasonic wave emission surface are in contact with each other, thus pushing air out toward the other end of the protective member. As a result, the protective member and the ultrasonic wave emission surface can be placed in intimate contact with each other.

In the one aspect of the present invention, the protective member preferably includes a reflector configured and arranged to reflect ultrasonic waves emitted from the ultrasonic wave emission surface.

In so doing, the reflector reflects the ultrasonic waves having been emitted from the ultrasonic wave emission surface, and the reflected ultrasonic waves return to the ultrasonic wave emission surface as ultrasonic echoes. Detection of the ultrasonic echoes by the ultrasonic probe body then makes it possible to carry out the adjustment process using the protective member including the reflector as an ultrasonic phantom.

In the one aspect of the present invention, the protective member is preferably formed of a gel material.

In so doing, when the attachment for an ultrasonic probe is being mounted, the protective member can be deformed so as to come into intimate contact with the ultrasonic wave emission surface.

Another aspect of the present invention relates to an ultrasonic probe including any of the attachments for an ultrasonic probe described above and the ultrasonic probe body.

In the other aspect of the present invention, a fitting section may be included that is configured and arranged to fit the ultrasonic probe body to the cover member in a state where the ultrasonic wave emission surface and the protective member are in intimate contact.

In so doing, the ultrasonic wave emission surface and the protective member can be reliably brought into intimate contact during mounting.

In the other aspect of the present invention, the ultrasonic wave emission surface of the ultrasonic probe body and the protective member of the attachment are preferably in intimate contact when the attachment is mounted onto the ultrasonic probe body.

In so doing, the ultrasonic waves emitted from the ultrasonic wave emission surface during the adjustment process are incident on the protective member without attenuation caused by the air, and thus an accurate adjustment process can be carried out.

Another aspect of the present invention relates to an ultrasonic probe including a head section and a processing apparatus. The head section includes an ultrasonic transducer device, the head section having an ultrasonic wave emission surface. The processing apparatus is configured and arranged to carry out transmission process and receipt process for the ultrasonic transducer device. The processing apparatus is further configured and arranged to carry out an adjustment process using as an ultrasonic phantom a protective member of an attachment for the ultrasonic probe when the attachment is mounted onto the ultrasonic probe. The protective member has a surface facing the ultrasonic wave emission surface and in contact with the ultrasonic wave emission surface.

According to the other aspect of the present invention, the processing apparatus can carry out the adjustment process using the protective member belonging to the attachment for an ultrasonic probe as an ultrasonic phantom, and thus the need to have already separately prepared an ultrasonic phantom for the adjustment process can be obviated, and the adjustment process can be readily carried out.

In the other aspect of the present invention, the processing apparatus is preferably configured and arranged to carry out the adjustment process using as the ultrasonic phantom the protective member as well as a cover member of the attachment when the attachment is mounted onto the ultrasonic probe, the cover member covering the ultrasonic wave emission surface.

In so doing, the processing apparatus can carry out the adjustment process using the protective member and the cover member as the ultrasonic phantom.

In the other aspect of the present invention, a detection unit may be included that is configured and arranged to detect mounting of the attachment onto the ultrasonic probe. The processing apparatus is preferably configured and arranged to carry out the adjustment process on a condition that the mounting is detected by the detection unit.

In so doing, the processing apparatus does not carry out the adjustment process in a case where the mounting has not been detected by the detection unit, and thus it is possible to prevent the adjustment process from being carried out in a state where the attachment for an ultrasonic probe has not been reliably mounted.

In the other aspect of the present invention, the processing apparatus is preferably configured and arranged to carry out a process for instructing that the mounting be done when the mounting is not detected by the detection unit.

In so doing, the processing apparatus can detect whether or not there has been mounting before the adjustment process, and can instruct that the mounting be done in a case where there has not been mounting, and thus the user can reliably mount the attachment for an ultrasonic probe.

In the other aspect of the present invention, the processing apparatus is preferably configured and arranged to carry out a process for instructing that the mounting be done when the mounting is not detected by the detection unit after a measurement process.

In so doing, the processing apparatus can detect whether or not there has been mounting after the measurement process, and can instruct that the mounting be done in a case where there has not been mounting, and thus the user can reliably mount the attachment for an ultrasonic probe.

Another aspect of the present invention relates to an electronic device including any of the ultrasonic probes described above.

Another aspect of the present invention relates to an ultrasonic diagnostic apparatus including any of the ultrasonic probes described above and a display unit for displaying image data for display.

BRIEF DESCRIPTION OF THE DRAWINGS

Referring now to the attached drawings which form a part of this original disclosure:

FIGS. 4A and 4B are an example of a basic configuration for an ultrasonic probe, and FIGS. 4C and 4D are a plan view and cross-sectional view of an attachment for an ultrasonic probe;

FIG. 6 is a drawing illustrating a first method for mounting an attachment for an ultrasonic probe;

DETAILED DESCRIPTION OF EXEMPLARY EMBODIMENTS

The following describes in greater detail a preferred embodiment of the present invention. The present embodiment described below is not, however, meant to gratuitously limit the content of the present invention described in the claims, nor is the entire configuration described in the present embodiment necessarily essential in terms of the solution of the present invention.

1. Ultrasonic Element

Figure 1A:
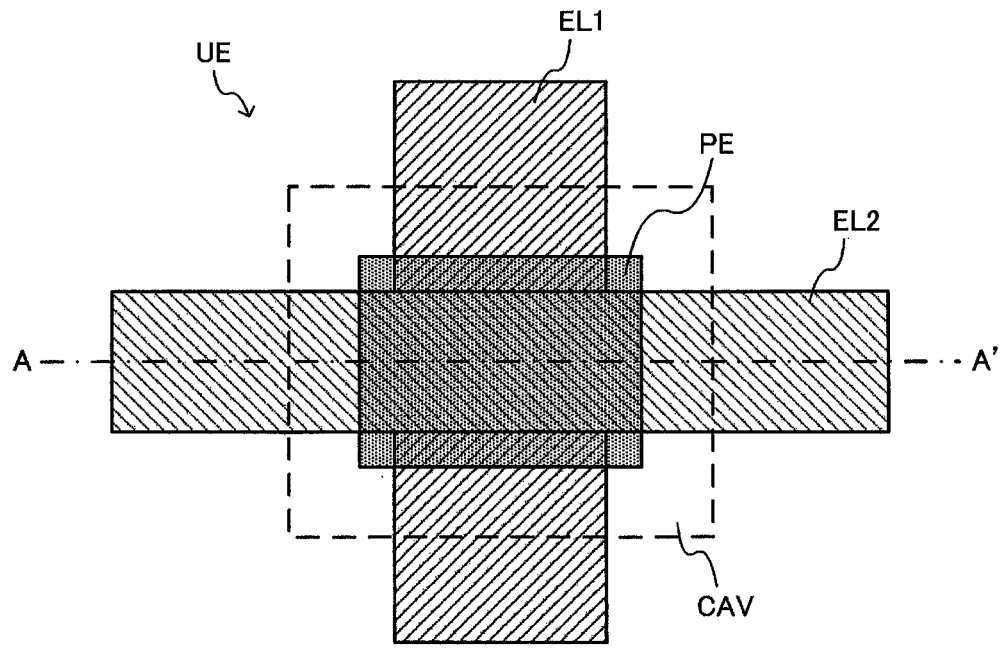
FIGS. 1A and 1B are an example of a basic configuration for an ultrasonic element.
Figure 1B:
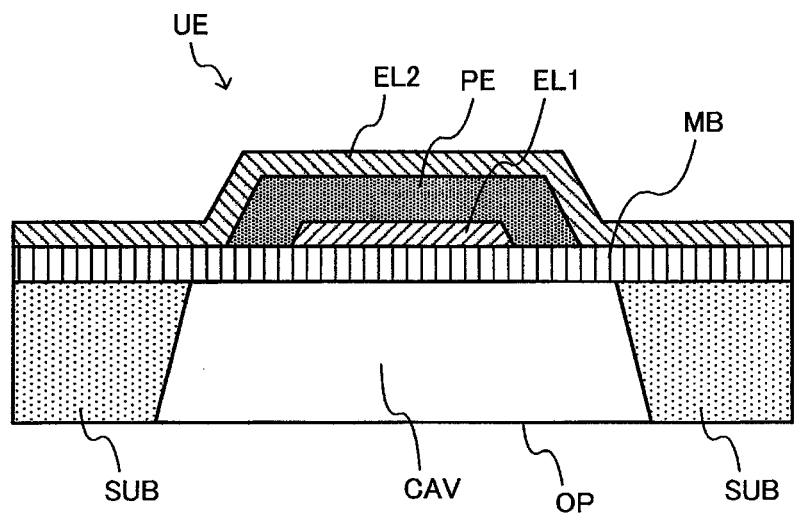

FIGS. 1A and 1B illustrate an example of a basic configuration for an ultrasonic element (ultrasonic transducer element) UE included in an ultrasonic probe of the present embodiment. The ultrasonic element UE of the present configuration example includes a vibrating membrane (membrane, support member) MB and a piezoelectric element section. The piezoelectric element section has a lower electrode (first electrode layer) EL1, a piezoelectric body film (a piezoelectric body layer) PE, and an upper electrode (a second electrode layer) EL2. The ultrasonic element UE of the present embodiment is not limited to being the configuration of FIGS. 1A and 1B, but rather a variety of modifications can be implemented, such as omitting a part of the constituent elements thereof, replacing same with other constituent elements, or adding other constituent elements.

FIG. 1A is a plan view of the ultrasonic element UE, which is formed on a substrate (a silicon substrate) SUB, the plan view being viewed from a direction perpendicular to the substrate on an element formation surface side. FIG. 1B is a cross-sectional view illustrating a cross-section taken along the A-A' line in FIG. 1A.

The first electrode layer EL1 is formed of, for example, a metal thin film on an upper layer of the vibrating membrane MB. The first electrode layer EL1 may be a wiring that extends to the outside of an element formation region, as illustrated in FIG. 1A, and is connected to an adjacent ultrasonic element UE.

The piezoelectric body film PE is formed of, for example, a lead zirconate titanate (PZT) thin film, and is provided so as to at least partially cover the first electrode layer EL1. The material of the piezoelectric body film PE, however, is not limited to being PZT, but rather, for example, lead titanate (PbTiO3), lead zirconate (PbZrO3), lanthanum lead titanate (Pb, La)TiO3), or the like may be used.

The second electrode layer EL2 is formed of, for example, a metal thin film, and is provided so as to at least partially cover the piezoelectric body film PE. The second electrode layer EL2 may be a wiring that extends to the outside of the element formation region, as illustrated in FIG. 1A, and is connected to an adjacent ultrasonic element UE.

The vibrating membrane (membrane) MB is provided so that an opening OP is closed off by a two-layered structure of, for example, an SiO2 thin film and a ZrO2 thin film. The vibrating membrane MB supports the piezoelectric body film PE and the first and second electrode layers EL1, EL2, and is also able to vibrate and generate ultrasonic waves according to contraction or expansion of the piezoelectric body film PE.

A cavity region CAV is formed by etching using reactive ion etching (RIE) or the like from a back surface of the silicon substrate SUB (the surface on which the element is not formed). Ultrasonic waves are emitted from an opening OP of the cavity region CAV.

The lower electrode of the ultrasonic element UE is formed of the first electrode layer EL1, and the upper electrode is formed of the second electrode layer EL2. More specifically, a portion of the first electrode layer EU covered by the piezoelectric body film PE forms the lower electrode, and a portion of the second electrode layer EL2 covering the piezoelectric body film PE forms the upper electrode. That is to say, the piezoelectric body film PE is provided sandwiched between the lower electrode and the upper electrode.

When a voltage is applied between the first electrode and the second electrode, i.e., between the first electrode layer EL1 and the second electrode layer EL2, the piezoelectric body film PE is thereby contracted or extended in the in-plane direction. One of the surfaces of the piezoelectric body film PE is bonded to the vibrating membrane MB via the first electrode layer EL1, while the second electrode layer EL2 is formed on the other surface, though no other layer is formed atop the second electrode layer EL2. For this reason, the side of the piezoelectric body film PE closer to the vibrating membrane MB is less readily contracted or expanded, and the side closer to the second electrode layer EL2 is more readily contracted or expanded. As such, when a voltage is applied to the piezoelectric body film PE, a flexure that is convex toward the cavity region CAV is created, causing the vibrating film MB to be flexed. Applying an alternating current voltage to the piezoelectric body film PE causes the vibrating membrane MB to vibrate with respect to a film thickness direction, and the vibration of the vibrating membrane MB causes ultrasonic waves to be emitted from the opening OP. The voltage (a drive voltage) applied to the piezoelectric body film PE is, for example, 10 to 30 V at peak-to-peak, and the frequency is, for example, 1 to 10 MHz.

The ultrasonic element UE operates also as a receiver element for receiving ultrasonic echoes occurring when emitted ultrasonic waves are reflected by an object and return. The ultrasonic echoes cause the vibrating membrane MB to vibrate, and this vibration applies a stress to the piezoelectric body film PE, producing a voltage between the lower electrode and the upper electrode. This voltage can be extracted as a receipt signal.

2. Ultrasonic Transducer Device

Figure 2:
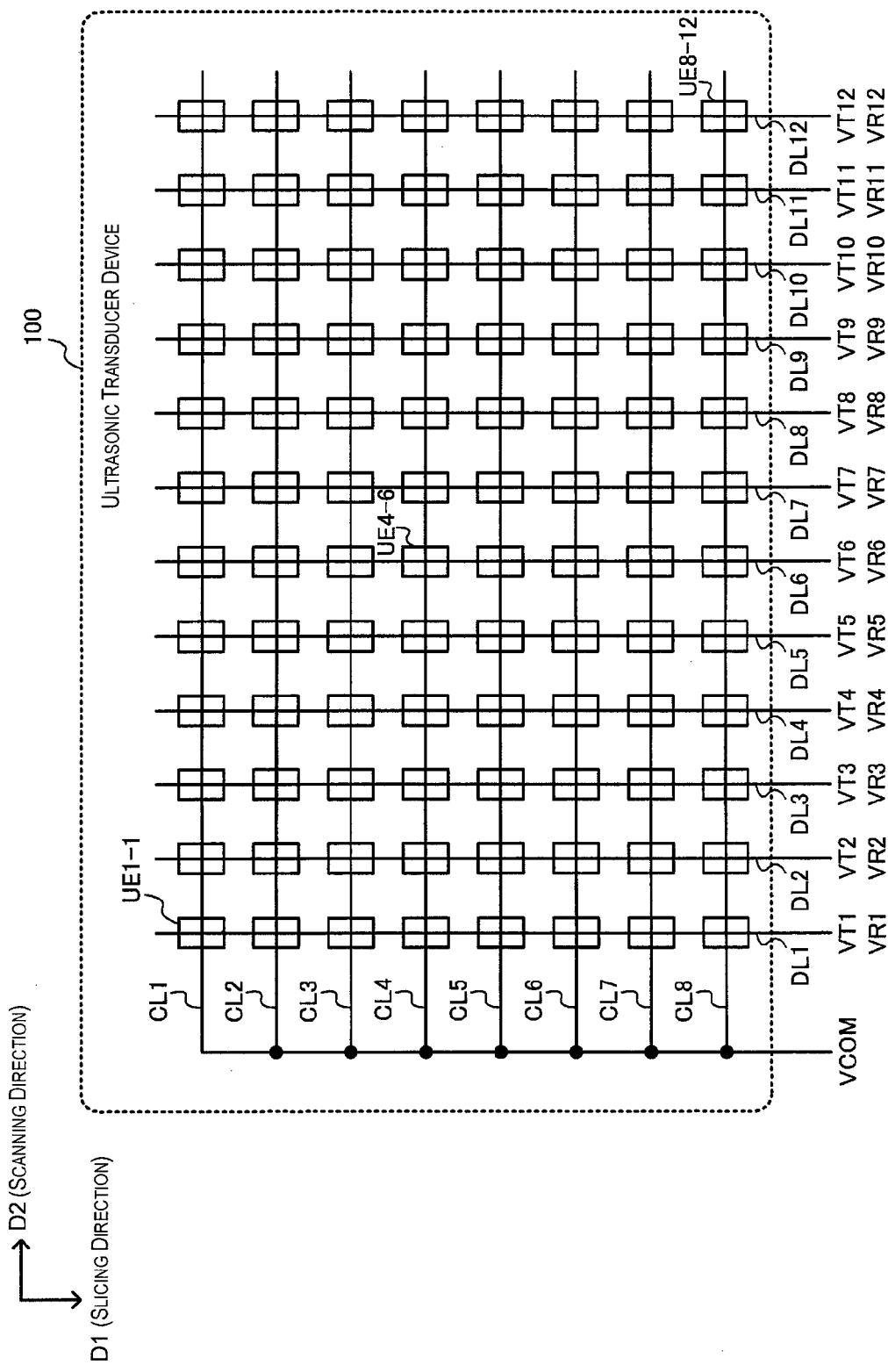
FIG. 2 is an example of a configuration for an ultrasonic transducer device.

FIG. 2 illustrates an example of a configuration for an ultrasonic transducer device 100 included in the ultrasonic probe of the present embodiment. The ultrasonic transducer device 100 of the present configuration example comprises a plurality of ultrasonic elements (ultrasonic transducer elements) UE), arranged in an arrayed shape; a first through n-th (where n is an integer 2 or greater) drive electrode lines DL1 to DLn, and a first through m-th (where m is an integer 2 or greater) common electrode line CL1 to CLm. FIG. 2 illustrates a case where m=8 and n=12, by way of example, but other values may be used. The ultrasonic transducer device 100 of the present embodiment is not limited to being the configuration of FIG. 2, but rather a variety of modifications can be implemented, such as omitting a part of the constituent elements thereof, replacing same with other constituent elements, or adding other constituent elements.

The plurality of ultrasonic elements UE are arranged in a matrix shape with m rows and n columns. For example, as illustrated in FIG. 2, the ultrasonic elements are arranged in eight rows along a first direction D1 and 12 columns along a second direction D2 that intersects with the first direction D1.

The ultrasonic elements UE can adopt, for example, the configuration illustrated in FIGS. 1A and 2B. In the description that follows, in a case where the position of an ultrasonic element UE within the array is to be specified, then, for example, an ultrasonic element UE positioned in the fourth row and the sixth column would be denoted by UE4-6. For example, eight ultrasonic elements UE1-6, UE2-6, . . . , UE7-6, UE8-6 are arranged in the sixth column. As another example, 12 ultrasonic elements UE4-1, UE4-2, . . . , UE4-11, UE4-12 are arranged in the fourth row.

The first through twelfth (more broadly, n-th) driving electrode lines DL1 to DL12 are wired along the first direction D1. Of the first through twelfth driving electrode lines DL1 to DL12, the j-th (where j is an integer $1 \leq j \leq 12$) driving electrode line DLj is connected to the first electrode belonging to each of the ultrasonic elements UE arranged in the j-th column.

During a transmission period for emitting ultrasonic waves, a first through twelfth transmission signal VT1 to VT12 outputted by a processing apparatus 200 (described below) are supplied to each of the ultrasonic elements UE via the drive electrode lines DL1 to DL12. During a reception period for receiving ultrasonic echo signals, receipt signals VR1 to VR12 coming from the ultrasonic elements UE are outputted to the processing device 200 via the drive electrode lines DL1 to DL12.

The first through eighth (more broadly, m-th) common electrode lines CL1 to CL8 are wired along the second direction D2. The second electrodes belonging to the ultrasonic elements UE are connected to any of the first through m-th common electrode lines CL1 to CLm. More specifically, for example, as illustrated in FIG. 2, an i-th (where i is an integer $1 \leq i \leq 8$) common electrode line CLi of the first through eighth common electrode lines CL1 to CL8 is connected to the second electrodes belonging to the ultrasonic electrodes UE arranged in the i-th column.

A common voltage VCOM is supplied to the first through eighth common electrode lines CL1 to CL8. The common voltage should be a constant direct current voltage, and need not be 0 V (a ground potential).

For example, as regards the ultrasonic element UE1-1 illustrated in FIG. 2, the first electrode is connected to the driving electrode line DL1, and the second electrode is connected to the first common electrode line CL1. As another example, as regards the ultrasonic element UE4-6 illustrated in FIG. 2, the first electrode is connected to the sixth driving electrode line DL6, and the second electrode is connected to the fourth common electrode line CIA.

The arrangement of the ultrasonic elements UE is not limited to being the matrix arrangement of m rows and n columns illustrated in FIG. 2. For example, the arrangement may be a so-called staggered arrangement in which m ultrasonic elements UE are arranged in odd-numbered ultrasonic element columns and m−1 ultrasonic elements UE are arranged in even-numbered ultrasonic element columns.

During the transmission period, the voltage of the difference between a transmission signal voltage and the common voltage is applied to each of the ultrasonic elements UE, and ultrasonic waves of a predetermined frequency radiate out. For example, the difference VT1-VCOM between a transmission signal voltage VT1 supplied to the drive electrode line DL1 and the common voltage VCOM supplied to the common electrode line CL1 is applied to the ultrasonic element UE1-1 in FIG. 2. Similarly, the difference VT6-VCOM between a transmission signal voltage VT6 supplied to the drive electrode line DL6 and the common voltage VCOM supplied to the common electrode line CL4 is applied to the ultrasonic element UE4-6.

3. Processing Apparatus

Figure 3:
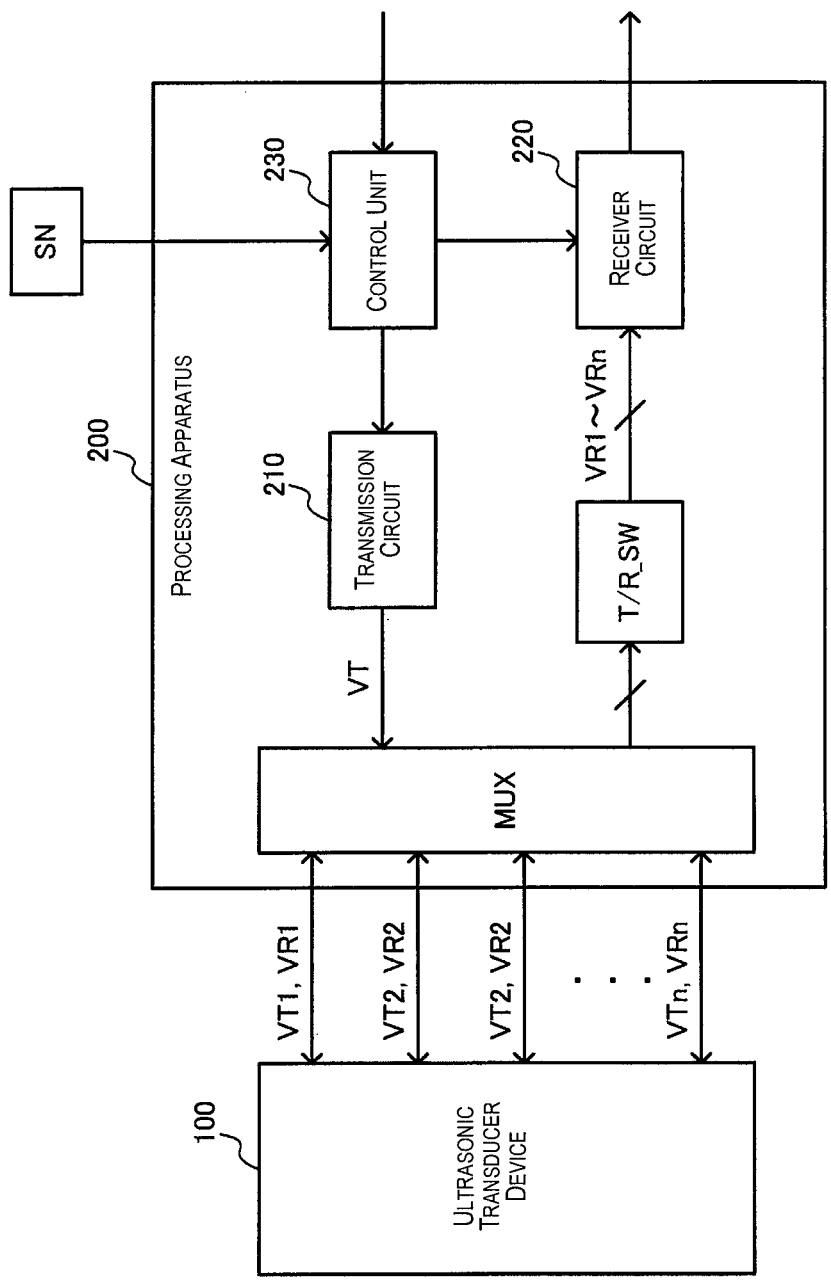
FIG. 3 is an example of a configuration for a processing apparatus.

FIG. 3 illustrates an example of a configuration for the processing apparatus 200 of the present embodiment. The processing apparatus 200 of the present configuration example comprises a transmission circuit 210, a receiver circuit 220, a control unit 230, a selection circuit MUX, and a transmission and receipt switching circuit T/R_SW. The processing apparatus 200 of the present embodiment is not limited to the configuration in FIG. 3, but rather a variety of modifications can be implemented, such as omitting a part of the constituent elements thereof, replacing same with other constituent elements, or adding other constituent elements.

The processing apparatus 200 carries out transmission processing and receipt processing for the ultrasonic transducer device 100. As shall be described below, in a case where an attachment for an ultrasonic probe has been mounted onto the ultrasonic probe, the processing apparatus 200 carries out an adjustment process, using the protective member belonging to the attachment for an ultrasonic probe as an ultrasonic phantom. This adjustment process shall be described in greater detail below.

The transmission circuit 210 outputs a transmission signal VT to the ultrasonic transducer device 100 via the selection circuit MUX during the transmission period. More specifically, the transmission circuit 210 generates the transmission signal VT on the basis of the control of the control unit 230, and outputs the transmission signal VT to the selection circuit MUX. The selection circuit MUX then selects at least one of the drive electrode lines DL1 to DLn belonging to the ultrasonic transducer device 100, on the basis of the control of the control unit 230, and outputs the transmission signal VT coming from the transmission circuit 210 to the selected drive electrode line(s). The frequency and amplitude voltage of the transmission signal VT can be set by the control unit 230.

The receiver circuit 220 carries out a process for receiving receipt signals VR1 to VRn coming from the ultrasonic transducer device 100. More specifically, the receiver circuit 220 receives during the transmission period the receipt signals VR1 to VRn coming from the ultrasonic transducer device 100, via the selection circuit MUX and the transmission and receipt switching circuit T/R_SW, and carries out receipt processes such as setting the amplitude and gain of the receipt signals, setting the frequency, and analog/digital conversion (A/D conversion). The result of the receipt processing is outputted to, for example, a processing unit 420 of an electronic device body 401 illustrated in FIG. 13, as detection data (detection information). The receiver circuit 220 can be constituted of, for example, a low-noise amplifier, a voltage control attenuator, a programmable gain amplifier, a low-pass filter, an A/D converter, and the like.

The control unit 230 controls the transmission circuit 210 and the receiver circuit 220. More specifically, the control circuit 230 controls the processing for generating and outputting the transmission signal VT with respect to the transmission circuit 220, and controls the frequency setting, gain, and the like of the receipt signals with respect to the receiver circuit 220. The control unit 230 is able to receive a detection signal coming from a detection unit SN belonging to the ultrasonic probe, and to determine whether or not the attachment for an ultrasonic probe has been mounted onto the ultrasonic probe on the basis of the detection signal. The processing apparatus 200 is then able to carry out the adjustment process, on the condition that mounting has been detected by the detection unit SN. The control unit 230 can be implemented with, for example, a field-programmable gate array (FPGA).

The selection circuit MUX selects at least one of the drive electrode lines DL1 to DLn belonging to the ultrasonic transducer device 100 on the basis of the control of the control unit 230. The transmission signal VT coming from the transmission circuit 210 is then outputted to the selected drive electrode line(s). For example, in a case where the selection circuit MUX has selected the drive electrode line DL1, then the transmission signal VT1 is outputted to the drive electrode line DL1 during the transmission period. The selection circuit MUX may select all of the n drive electrode lines DL1 to DLn at the same timing or may select one drive electrode line at a time, for example in an order such as DL1, DL2, DL3, . . . , and so forth.

The transmission and receipt switching circuit T/R_SW includes n switch elements, and switches the transmission signal VT and the receipt signals VR1 to VRn on the basis of the control of the control unit 230. More specifically, the n switch elements are set to an OFF state during the transmission period, thereby preventing the transmission signal VT having been outputted from the transmission circuit 210 from being inputted into the receiver circuit 220, and the n switch elements are set to an ON state during the reception period, thereby causing the receipt signals VR1 to VRN coming from the ultrasonic transducer device 100 to be inputted to the receiver circuit 220.

4. Ultrasonic Probe and Attachment for Ultrasonic Probe

FIGS. 4A and 4B illustrate an example of a basic configuration for an ultrasonic probe 300 of the present embodiment. The ultrasonic probe 300 includes an ultrasonic probe body 310 and an attachment 320 for an ultrasonic probe. The ultrasonic probe body 310 includes the processing apparatus 200 and a head section 311. The ultrasonic probe 300 of the present embodiment is not limited to being the configuration of FIGS. 4A and 4B, but rather a variety of modifications can be implemented, such as omitting a part of the constituent elements thereof, replacing same with other constituent elements, or adding other constituent elements.

The head section 311 is detachable from the processing apparatus 200, where FIG. 4A illustrates a case where the head section 311 is connected to the processing apparatus 200 and FIG. 4B illustrates a case where the head section 311 is separated from the processing apparatus 200.

The processing apparatus 200 is connected to the head section 311 via a connector 150. More specifically, connecting a processing apparatus-side connector 150b and a head section-side connector 150a causes the processing apparatus 200 and the head section 311 to be connected to each other. The processing apparatus 200 is connected to an electronic device (ultrasonic diagnostic apparatus) body by a cable 312.

The head section 311 includes the ultrasonic transducer device 100, a support member 160, a contact member 130 in contact with a subject, a protective film 170, the connector 150a, and a head section housing 140. The ultrasonic transducer device 100 is provided between the contact member 130 and the support member 160.

The support member 160 is a member for supporting the ultrasonic transducer device 100. The protective film 170 is provided to a reverse side of the ultrasonic transducer device 100 (the side to which the opening OP is provided in FIG. 1B), and protects the ultrasonic transducer device 100.

FIG. 4C is a plan view of a case where an inner surface of a cover member 321 is viewed from an opening 323 of the attachment 320 for an ultrasonic probe. FIG. 4D is a cross-sectional view illustrating a cross-section taken along the G-G' line in FIG. 4C.

The attachment 320 for an ultrasonic probe includes the cover member 321 and the protective member 322. The cover member 321 covers an ultrasonic wave emission surface 131 of the head section 311 of the ultrasonic probe body 310 in a state where the attachment 320 for an ultrasonic probe is mounted onto the ultrasonic probe body 310. The cover member 321 includes the opening 323, into which the ultrasonic probe body 310 is inserted during mounting. The protective member 322 is provided to a side of the cover member 321 opposite to (facing) the ultrasonic wave emission surface 131, and is contact with the ultrasonic wave emission surface 131 in a state where the attachment 320 for an ultrasonic probe is mounted onto the ultrasonic probe body 310.

The ultrasonic wave emission surface 131 is a surface from which ultrasonic waves are emitted in the head section 311. The ultrasonic wave emission surface 131 may be a flat surface or may be a curved surface.

Either the protective member 322 or the protective member 322 and the cover member 321 constitutes the ultrasonic phantom for the adjustment process of the ultrasonic probe body 310. Herein, an "ultrasonic phantom" is an ultrasonic wave propagator in which a reflector of ultrasonic waves is arranged. An "ultrasonic wave propagator" is, for example, a liquid, solid, gel, or the like that has lower ultrasonic wave attenuation properties than air (a gas). In the attachment 320 for an ultrasonic probe of the present embodiment, the protective member 322 is the ultrasonic wave propagator.

When the subject of the ultrasonic probe 300 is, for example, a human body, then the ultrasonic phantom preferably has properties close to those of human tissue. Therefore, the protective member preferably has the same sound propagation speed and acoustic impedance as the human body, and the cover member 321 and the reflector preferably have the same acoustic impedance as, for example, bone, internal organs, and the like.

An attachment (cover) not equipped with an ultrasonic wave propagator may include a surface (reflecting surface) facing the ultrasonic wave emission surface 131 with a layer of air interposed therebetween, but air causes intense attenuation, making it difficult to carry out the adjustment process. By contrast, in the attachment 320 for an ultrasonic probe of the present embodiment, the ultrasonic phantom is constituted of: the protective member 322, which has the ability to propagate ultrasonic waves, i.e., has lower attenuation properties than the attenuation properties of air; and the cover member 321, which retains a surface (end surface) facing a surface (end surface) of the protective member 322 in contact with the ultrasonic wave emission surface 131. Having the protective member 322 in intimate contact with the inner surface of the cover member 321 causes the inner surface of the cover member 321 to be a reflecting surface.

As a modification example of the attachment 320 for an ultrasonic probe, an intermediate support member for regulating the end surface shape of the protective member 322 may be provided between the protective member 322 and the inner surface of the cover member 321. The intermediate support member may be entirely in intimate contact with the end surface of the protective member 322. For example, providing a hollow ring-shaped intermediate support member causes the protective member 322 to be pushed against the hollow section and causes the end surface shape of the protective member to become a predetermined flat surface (or spherical surface). An ultrasonic phantom where the interface between the air of the hollow section and the protective member 322 becomes the reflecting surface is thus formed.

Figure 5C:
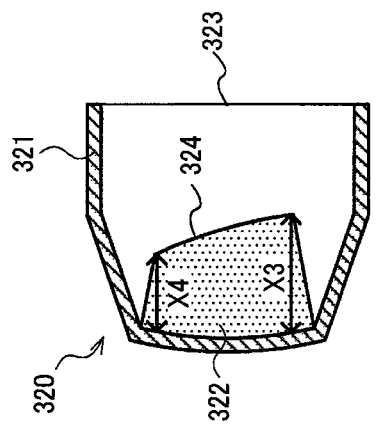
FIGS. 5A, 5B, and 5C are a cross-sectional view of an attachment for an ultrasonic probe.
Figure 5B:
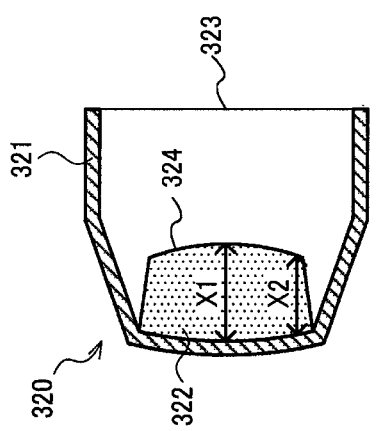
Figure 5A:
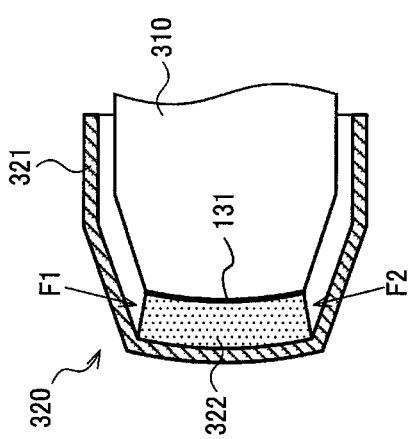

FIGS. 5A, 5B, and 5C are cross-sectional views of the attachment 320 for an ultrasonic probe of the present embodiment. FIG. 5A is a cross-sectional view of a state where the attachment 320 for an ultrasonic probe has been mounted onto the ultrasonic probe body 310. As illustrated in FIG. 5A, in the state where the attachment 320 for an ultrasonic probe has been mounted onto the ultrasonic probe body 310, the protective member 322 is in intimate contact with the ultrasonic wave emission surface 131. That is to say, the protective member 322 is formed of a shape and material in intimate contact with the ultrasonic wave emission surface 131 during mounting. The material of the protective member 322 is, for example, a gel material, and is more preferably self-adsorptive. To enhance adhesion, the protective member 322 may also be coated with a gel.

So doing makes it possible to bring the protective member 322 and the ultrasonic wave emission surface 131 in intimate contact and prevents air or the like from entering in a gap between the two, and thus makes it possible to carry out a higher-precision adjustment process in a case where the protective member 322 is used as the ultrasonic phantom. The entire surface of the ultrasonic wave emission surface 131 is more preferably in intimate contact with the protective member 322. So doing causes the ultrasonic waves emitted from the entire surface of the ultrasonic wave emission surface 131 to be incident on the protective member during the adjustment process, and thus makes it possible to carry out a more accurate adjustment process.

FIGS. 5B and 5C illustrate examples of the shape (cross-sectional shape) of the protective member 322 before the attachment 320 for an ultrasonic probe has been mounted onto the ultrasonic probe body 310. In the protective member 322 illustrated in FIG. 5B, an opposing surface 324 to the ultrasonic wave emission surface 131 has a convex shape, and in the protective member 322 illustrated in FIG. 5C, the opposing surface 324 to the ultrasonic wave emission surface 131 has an inclined shape. The shape of the protective member 322 is not limited to being the shapes illustrated in FIGS. 5B and 5C.

For the opposing surface 324 to have a convex shape means a shape such that in a case where the direction in which the ultrasonic probe body 310 is inserted is understood to be the thickness direction, the thickness is greater at a center section of the opposing surface 324, and the thickness becomes gradually smaller going toward the peripheral edge section. For example, in FIG. 5b, the thickness is X1 at the center section, and the thickness is X2 (where X1>X2) at the peripheral edge section.

For the opposing surface 324 to be an inclined surface means a shape such that in a case where the direction in which the ultrasonic probe body 310 is inserted is understood to be the thickness direction, the thickness is greater at one end of the opposing surface 324, and the thickness becomes gradually smaller going toward the other end. For example, in FIG. 5C, the thickness is X3 at one end, and the thickness is X4 (where X3>X4) at the other end.

As illustrated in F1 and F2 in FIG. 5A, one end surface of the protective member 322 (the end surface not in contact with the ultrasonic wave emission surface 131) is mounted to the inner surface of the cover member 321, whereas the side surface of the protective member 322 have separated from the inner surface of the cover member 321. This manner of providing to at least one side of the side surface section a space where the protective member 322 can be readily deformed when the head section 311 of the ultrasonic probe body 310 is pressed against and is in intimate contact with the protective member 322 makes it possible to relieve stress applied to the cover member 321 or to the head section 311, and to reduce the risk of damage thereto. The same is also true of FIGS. 5B and 5C, as well as FIGS. 6 to 8 described below.

FIG. 6 is a drawing illustrating a first method for mounting the attachment 320 for an ultrasonic probe. The convex shape illustrated in FIG. 5B shall be described by way of example as the shape of the protective member 322. When the attachment 320 for an ultrasonic probe is to be mounted onto the ultrasonic probe body 310, first, the ultrasonic wave emission surface 131 and a convex section of the protective member 322 come into contact with each other, as illustrated by A1 in FIG. 6. When the head section 311 of the ultrasonic probe body 310 is further inserted inside of the cover member 321, the surface of contact spreads, as illustrated by A2 and A3 in FIG. 6, and air is pushed out to the exterior together therewith. The protective member 322 and the full surface of the ultrasonic wave emission surface 131 are thus in intimate contact with each other, as illustrated by A4 and A5 in FIG. 6.

Figure 7B:
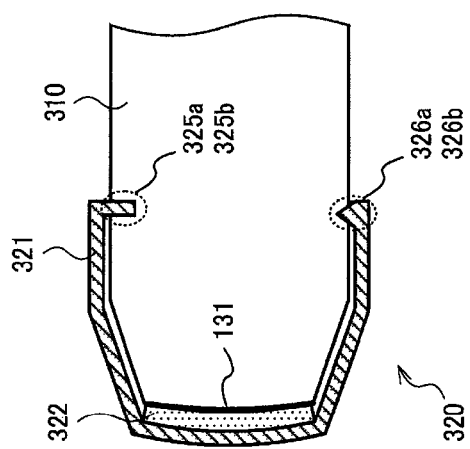
FIGS. 7A and 7B are drawings illustrating a second and third method for mounting an attachment for an ultrasonic probe.
Figure 7A:
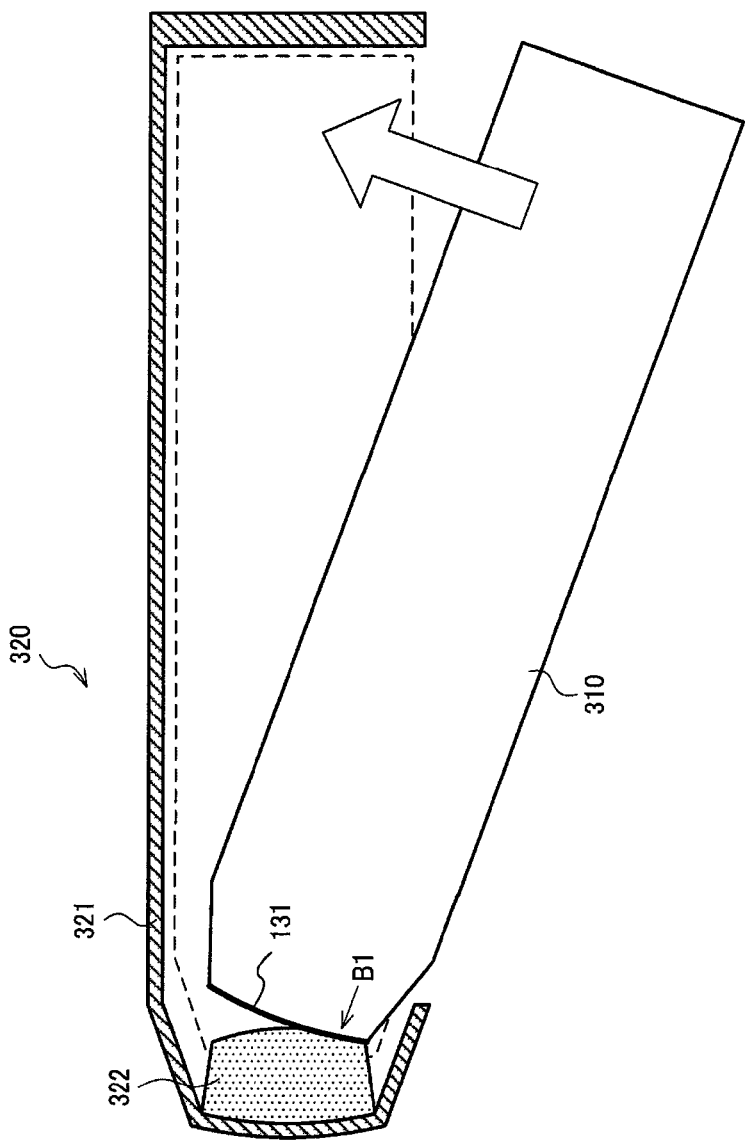

FIGS. 7A and 7B are drawings illustrating a second and third method for mounting the attachment 320 for an ultrasonic probe. In the second method of mounting illustrated in FIG. 7A, for example, the protective member 322 having the inclined shape illustrated in FIG. 5C is used. As illustrated by B1 in FIG. 7A, first the ultrasonic wave emission surface 131 and the one end of the protective member 322 are in contact, and then the surface of contact spreads toward the other end of the protective member 322, and air is pushed out to the exterior together therewith. In the state where the ultrasonic probe body 310 is housed inside of the cover member 321 (illustrated by the wavy line), then, the protective member 322 and the full surface of the ultrasonic wave emission surface 131 are in intimate contact.

In the third method of mounting illustrated in FIG. 7B, more specifically, the cover member 321 (more broadly, the attachment 320 for an ultrasonic probe) includes fitting sections 325a, 326a by which the ultrasonic probe body 310 is fitted to the cover member 321 in the state where the ultrasonic wave emission surface 131 and the protective member 322 are in intimate contact with each other during mounting. The ultrasonic probe body 310, too, includes fitting sections 325b, 326b that are fitted to the fitting sections 325a, 326a, respectively, of the cover member 321. First fitting the fitting sections 325a and 325b causes the one end of the protective member 322 and the ultrasonic wave emission surface 131 to come into contact with each other. Then finally fitting the fitting sections 326a and 326b causes the protective member 322 and the full surface of the ultrasonic wave emission surface 131 to come into intimate contact with each other.

In this manner, according to the attachment 320 for an ultrasonic probe of the present embodiment, the protective member 322 and the full surface of the ultrasonic wave emission surface 131 can be brought into intimate contact with each other, and thus the ultrasonic wave emission surface 131 can be reliably protected from impacts or the like, and moreover a higher-precision adjustment process can be carried out in a case where the protective member 322 is used as an ultrasonic phantom for the adjustment process.

Figure 8A:
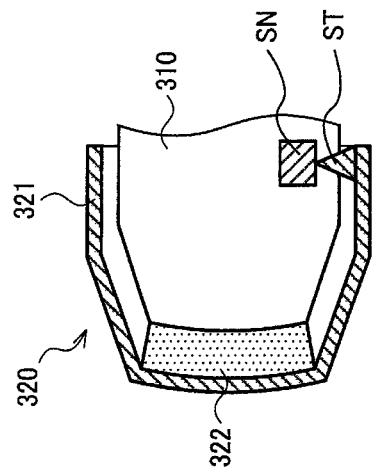
FIGS. 8A and 8B are an example of a configuration for a detection unit.
Figure 8B:
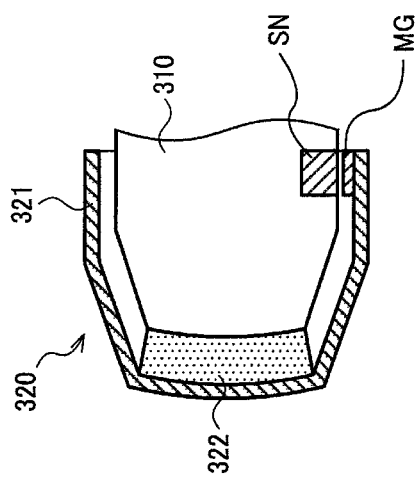

FIGS. 8A and 8B illustrate an example of a configuration for the detection unit SN for detecting the mounting of the attachment 320 for an ultrasonic probe onto the ultrasonic probe body 310 (more broadly, the ultrasonic probe).

The configuration example for the detection unit SN illustrated in FIG. 8A is a magnetic sensor, and detects a magnetic flux density produced by a magnet provided to a position facing the magnetic sensor on the cover member 321. The magnetic flux density will be greater in a case where the attachment 320 for an ultrasonic probe has been mounted onto the ultrasonic probe body 310, and thus detecting the change in the magnetic flux density allows the magnetic sensor SN to detect the mounting.

The configuration example for the detection unit SN illustrated in FIG. 8B is a mechanical switch, and contact of a protruding section ST provided to the cover member 321 with the mechanical switch SN enables detection of the mounting.

The processing apparatus 200 carries out the adjustment process, on the condition that mounting has been detected by the detection unit SN. The processing apparatus 200 also carries out a process for instructing mounting in a case where mounting is not detected by the detection unit SN.

In this manner, according to the attachment 320 for an ultrasonic probe of the present embodiment, the processing apparatus 200 does not carry out the adjustment process in a case where mounting has not been detected by the detection unit SN, and thus it is possible to avoid prevent the adjustment process from being carried out in a state where the attachment 320 for an ultrasonic probe has not been reliably mounted. In a case where the attachment 320 for an ultrasonic probe is not mounted, mounting can be instructed to the user by the processing apparatus 200, and thus the user can reliably mount the attachment 320 for an ultrasonic probe.

Figure 9:
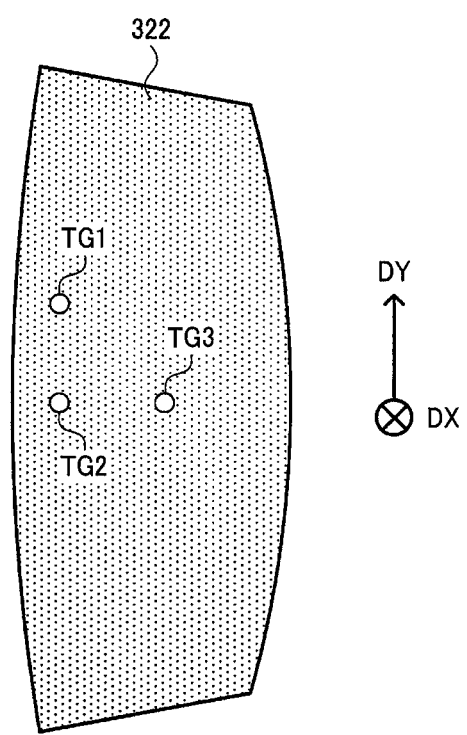
FIG. 9 is an example of a configuration for a target arranged in the interior of a protective member.

FIG. 9 illustrates an example of a configuration for targets (more broadly, reflectors) arranged in the interior of the protective member 322, equivalent to the cross-section illustrated in FIG. 5B. The targets illustrated in FIG. 9 comprise three targets TG1, TG2, TG3. The targets TG1, TG2, TG3 are objects for the adjustment process of the ultrasonic probe body 310, and can be constituted of, for example, wires or the like. The targets provided to the interior of the protective member 322 of the present embodiment are not limited to being the configuration of FIG. 9, but rather a variety of modifications can be implemented, such as omitting a part of the constituent elements thereof, replacing same with other constituent elements, or adding other constituent elements.

The targets TG1 and TG2 are two wires arranged along, for example, the DX direction in FIG. 9 so that, in the state where the protective member 322 is mounted so as to press against (be in intimate contact with) the ultrasonic wave emission surface 131 of the ultrasonic probe body 310, the distances from the ultrasonic wave emission surface 131 are the same, and so as to be separated in a predetermined direction (for example, the DY direction in FIG. 9) and also be parallel. The targets TG2 and TG3 are two wires arranged along, for example, the DX direction in FIG. 9 so as to be separated so that the distances from the ultrasonic wave emission surface 131 are different and so as to be in parallel, at positions substantially overlapping in the in-plane direction (for example, the DY direction in FIG. 9) of the plane (element array plane) in which the ultrasonic elements UE of the ultrasonic transducer device 100 are arrayed, in the state where the protective member 322 is mounted so as to press against (be in intimate contact with) the ultrasonic wave emission surface 131.

When the attachment 320 for an ultrasonic probe is correctly mounted onto the ultrasonic probe body 310, the ultrasonic wave emission surface 131 of the head section 311 is in intimate contact with the protective member 322, as described above. When ultrasonic waves are emitted in this mounted state, the targets TG1, TG2, TG3 reflect the ultrasonic waves emitted from the ultrasonic wave emission surface 131, and the reflected ultrasonic waves return to the ultrasonic wave emission surface 131 as ultrasonic echoes. Detecting the ultrasonic echoes allows the ultrasonic probe body 310 to carry out the adjustment process using the protective member 322, which includes the targets TG1, TG2, TG3, as the ultrasonic phantom.

In addition to two examples described below (FIGS. 11 and 12), the adjustment process could be, for example, to use the targets TG1 and TG2 to adjust the resolution in a scanning direction (for example, the D2 direction in FIG. 2) or a slicing direction (for example, the D1 direction in FIG. 2). Alternatively, it would be possible to adjust the focal point of an emitted ultrasonic beam. It would also be possible to use the targets TG2 and TG3 to adjust the resolution (temporal resolution) in the depth direction. It would alternatively be possible to adjust the recording cycle for the receipt signals.

In this manner, according to the attachment 320 for an ultrasonic probe of the present embodiment, the adjustment process of the ultrasonic probe body 310 can be carried out using the protective member 322 or the like as the ultrasonic phantom when the attachment 320 for an ultrasonic probe has been mounted, and thus the need to have already separately prepared an ultrasonic phantom for the adjustment process can be obviated and the ultrasonic process can be carried out easily and with a simple configuration.

The function of the ultrasonic phantom can also be implemented with the protective member 322 alone, or can be implemented with the protective member 322 and the cover member 321. Alternatively, the ultrasonic phantom can also be implemented with the protective member 322 comprising the reflectors. The ultrasonic phantom can further be implemented with the protective member 322 comprising the reflectors and the cover member 321.

In a case where the attachment 320 for an ultrasonic probe of the present embodiment were not to be used, it would be necessary to separately prepare an ultrasonic phantom or the like to carry out the adjustment process for the ultrasonic probe. In the case of, for example, a portable ultrasonic diagnostic apparatus, however, it would be inconvenient for the user to have to carry the ultrasonic phantom together with the portable diagnostic apparatus at all times, and so doing would also compromise the advantages of portability. When the ultrasonic phantom is used to carry out the adjustment process with less frequency, it becomes more difficult to maintain the performance of the ultrasonic probe in a desired state at all times.

According to the attachment 320 for an ultrasonic probe of the present embodiment, however, the adjustment process can be carried out reliably and easily before diagnosis in a portable diagnostic apparatus or the like, and thus accurate and highly reliable diagnoses or the like become possible.

Figure 10:
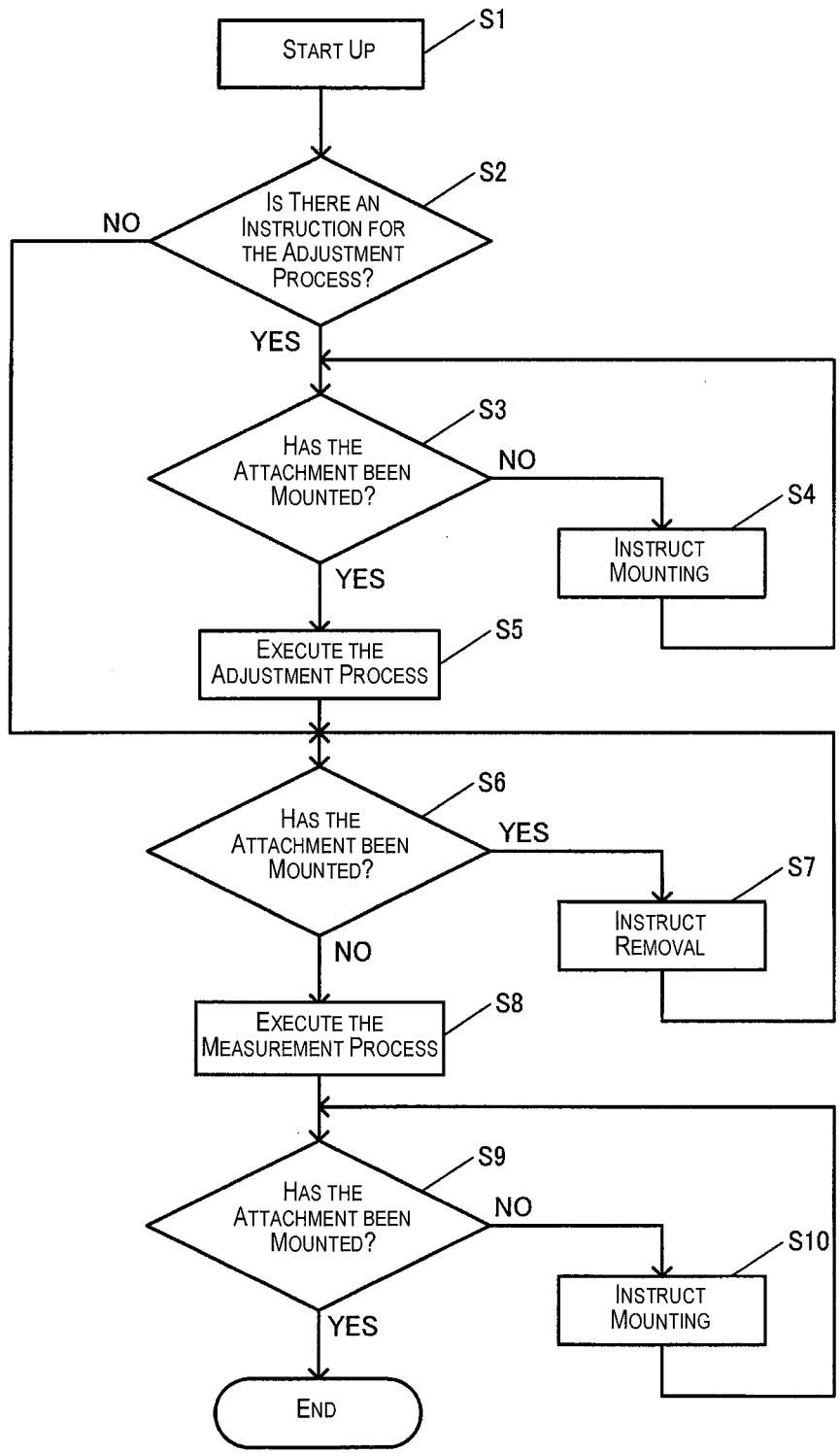
FIG. 10 is a flow chart illustrating one example of a process executed by an ultrasonic probe.

FIG. 10 is a flow chart illustrating one example of the process executed by the ultrasonic probe 300 (the ultrasonic probe body 310 and the attachment 320 for an ultrasonic probe) of the present embodiment. The flow illustrated in FIG. 10 is controlled by the control unit 230 of the processing apparatus 200 (FIG. 3), and the adjustment process as well as a measurement process are executed by the transmission circuit 210 and the receiver circuit 220 on the basis of the control of the control unit 230.

First, the electronic device, including the ultrasonic probe 300, is started up, and in association therewith the processing apparatus 200 of the ultrasonic probe 300 is started up (step S1). Next, the control unit 230 determines whether or not there has been an instruction for the adjustment process (step S2). An instruction for the adjustment process may be, for example, an instruction that is based on a command input by a user, or may be an instruction that is previously set so that the adjustment process is executed after start up. More specifically, the instruction fort the adjustment process is issued by a main control unit 410 of an electronic device body 401 (FIG. 13) to the control unit 230. In a case where there has been an instruction for the adjustment process, the flow proceeds to step S3; in a case where there has not been an instruction for the adjustment process, the flow jumps to step S6 without the adjustment process being executed.

In step S3, the control unit 230 determines whether or not the attachment 320 for an ultrasonic probe has been mounted on the basis of the detection signal coming from the detection unit SN. In a case where the attachment 320 for an ultrasonic probe has not been mounted, the user is instructed to mount same (step S4). That is to say, the processing apparatus 200 carries out a process for instructing mounting in a case where mounting is not detected by the detection unit SN. This instruction to mount can be carried out by, for example, displaying a message prompting mounting or the like on a display unit 440, via the main control unit 410 of the electronic device body 401. In a case where the attachment 320 for an ultrasonic probe has been mounted, the control unit 230 controls the adjustment process, and the adjustment process is executed (step S5). That is to say, the processing apparatus 200 carries out the adjustment process on the condition that mounting has been detected by the detection unit SN.

After the execution of the adjustment process, the control unit 230 determines whether or not the attachment 320 for an ultrasonic probe has been mounted on the basis of the detection signal coming from the detection unit SN (step S6). This is one because the attachment 320 for an ultrasonic probe needs to be removed before the measurement process can be executed. In a case where the attachment 320 for an ultrasonic probe is mounted, the user is instructed to remove same (step S7). In a case where the attachment 320 for an ultrasonic probe is not mounted, the control unit 230 controls the measurement process, and the measurement process is executed (step S8).

After the execution of the measurement process, the control unit 230 determines whether or not the attachment 320 for an ultrasonic probe is mounted on the basis of the detection signal coming from the detection unit SN (step S9). This is done in order to protect the head section 311, in particular the ultrasonic transducer device 100, by mounting the attachment 320 for an ultrasonic probe after the measurement. In a case where the attachment 320 for an ultrasonic probe is not mounted, the user is instructed to mount same (step S10), and in a case where the attachment 320 for an ultrasonic probe is mounted, then the process is terminated.

In this manner, according to the ultrasonic probe 300 of the present embodiment, whether or not the attachment 320 for an ultrasonic probe has been mounted is detected before the adjustment process or after the measurement process, and an instruction for mounting can be issued in a case where the attachment 320 for an ultrasonic probe is not mounted; the user is thus able to reliably mount the attachment 320 for an ultrasonic probe. Further, the processing apparatus 200 does not carry out the adjustment process in a case where mounting is not detected by the detection unit SN, and thus it is possible to prevent the adjustment process from being carried out in a state where the attachment 320 for an ultrasonic probe has not been reliably mounted. Further, an instruction for removal can be issued in a case where the attachment 320 for an ultrasonic probe is mounted prior to the measurement process, and it is possible to prevent the user from accidentally taking measurements while the attachment 320 for an ultrasonic probe remains mounted.

Figure 11:
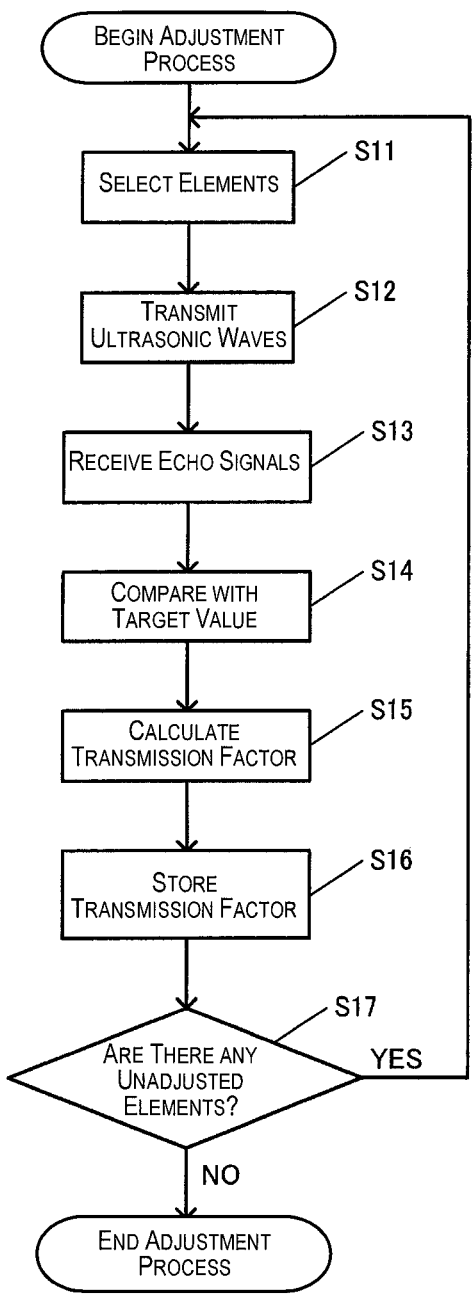
FIG. 11 is a flow chart illustrating a first example of an adjustment process executed by an ultrasonic probe.

FIG. 11 is a flow chart illustrating a first example of the adjustment process executed by the ultrasonic probe 300 of the present embodiment. The first example is a process for adjusting the variance in intensity of the ultrasonic waves emitted from the ultrasonic elements. More specifically, the transmission signal VT having a predetermined amplitude voltage is supplied to the ultrasonic elements in a state where the attachment 320 for an ultrasonic probe has been mounted, ultrasonic waves are transmitted, and the ultrasonic echoes reflected by the targets (objects) in the interior of the protective member 322 are received. The signal level (signal intensity) of the received echo signals is proportional to the intensity of the ultrasonic waves emitted, and thus the control unit 230 compares the signal level with a target value (reference value), and can calculate a transmission factor TCF so as to correct for a deviation from the target value. The control unit 230 has stored the transmission factor TCF calculated for each of the ultrasonic elements, and in the measurement process the transmission factor TCF stored for each of the ultrasonic elements is used to set the amplitude voltage of the transmission signal VT. So doing makes it possible to reduce the variance in the ultrasonic wave intensity between each of the elements.

A case where the target value for a receipt signal level is 10 mV when a transmission signal VT for which the predetermined amplitude voltage is 5V is applied shall now be described by way of example. When, for a given ultrasonic element, the signal level that is actually received is 8 mV, the transmission factor TCF of that element is TCF=10/8=1.25. The amplitude voltage of the transmission signal VT for when that element is to be driven is set to TCF×5 V=1.25×5 V=6.25 V, whereby a receipt signal level of the target value 10 mV is obtained. When, for a given ultrasonic element, the signal level that is actually received is 12 mV, the transmission factor TCF of that element is TCF=10/12=0.833. The amplitude voltage of the transmission signal VT for when that element is to be driven is set to TCF×5 V=0.833×V=4.165 V, whereby a receipt signal level of the target value 10 mV is obtained.

First, an ultrasonic element intended for adjustment is selected (step S11). Adjustment may be directed to individual ultrasonic elements, or may be directed to an ultrasonic element column including a plurality of ultrasonic elements. For example, in the ultrasonic transducer device 100 illustrated in FIG. 2, one of the first through twelfth ultrasonic element columns could be selected. An ultrasonic element column refers to a column constituted of a plurality of ultrasonic elements that are connected to the same drive electrode line. For example, the sixth ultrasonic element column is constituted of eight ultrasonic elements UE1-6, UE2-6, . . . , UE8-6 that are connected to the drive electrode line DL6. The selection of the ultrasonic element column is carried out by the selection circuit MUX on the basis of the control of the control unit 230.

Next, the transmission circuit 210 outputs the transmission signal VT to the selected ultrasonic elements (ultrasonic element column, and the selected ultrasonic elements (ultrasonic element column) transmit ultrasonic waves (step S12). Then, the ultrasonic transducer device 100 receives the echo signals, and the receipt signals VR1 to VR12 are inputted to the receiver circuit 220 (step S13). The receiver circuit 220 outputs signal level information (ultrasonic wave intensity information) on the receipt signals to the control unit 230.

The control unit 230 compares the signal level information with the target value (step 14). More specifically, the signal level information is digital values corresponding to the signal levels (voltage values) of the receipt signals. The control unit 230 then calculates the transmission factor TCF on the basis of the results from comparing the signal level information and the target value (step S15), and stores the calculated transmission factor TCF in a non-volatile storage apparatus provided to the control unit 230 or the like (step S16).

Next, the control unit 230 determines whether or not there are any unadjusted elements (is no unadjusted element column) (step S17); in a case where there are unadjusted elements (is no unadjusted element column), then the flow returns to step S11, and elements (an element column) intended for the next adjustment are selected. In a case where there are no unadjusted elements (is no unadjusted element column), then the adjustment process is terminated.

Figure 12:
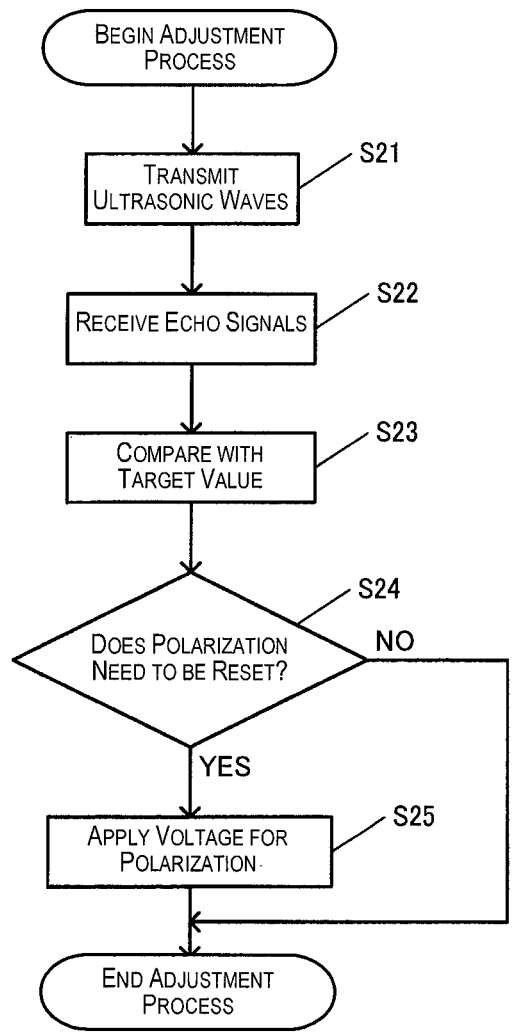
FIG. 12 is a flow chart illustrating a second example of an adjustment process executed by an ultrasonic probe.

FIG. 12 is a flow chart illustrating a second example of the adjustment process executed by the ultrasonic probe 300 of the present embodiment. The second example is a process for resetting the polarization of the piezoelectric body film PE (FIGS. 1A, 1B) of the ultrasonic elements. The piezoelectric body films PE of each of the ultrasonic elements are, at the time of factory shipment, set to a uniformly polarized state, but in some instances the polarization is reduced when, for example, temperatures become high or for some reason a high voltage is applied. When the polarization is reduced, the intensity of the ultrasonic waves emitted is reduced, but the adjustment process of the first example described above, i.e., the transmission factor TCF makes it possible to correct the ultrasonic wave intensity when the reduction in polarization is small. When the reduction in polarization is considerable, however, it becomes difficult to correct the ultrasonic wave intensity using the transmission factor TCF. Even in such a case, resetting the polarization of each of the ultrasonic elements by the adjustment process of the second example makes it possible to achieve uniformity in the polarization of each of the elements.

First, the transmission circuit 210 outputs the transmission signal VT to the ultrasonic elements, and the ultrasonic elements transmit the ultrasonic waves (step S21). In this case, the ultrasonic transducer device 100 outputs the transmission signal VT to all of the ultrasonic elements. Then, the ultrasonic transducer device 100 receives the echo signals, and the receipt signals VR1 to VR12 are inputted to the receiver circuit 220 (step S22). The receiver circuit 220 outputs the signal level information (ultrasonic wave intensity information) on the receipt signals to the control unit 230.

The control unit 230 compares the signal level information with the target value (reference value) (step S23), and determines whether or not the polarization needs to be reset on the basis of the result from comparing the signal level information and the target value (step S24). More specifically, in a case where the receipt signal level is lower than the target value, the transmission circuit 210 outputs a voltage for polarization to each of the ultrasonic elements on the basis of the control of the control unit 230. The voltage for polarization is a voltage by which the piezoelectric body films PE of each of the elements can be uniformly polarized, and is a higher voltage than that of the transmission signal VT of when the ultrasonic waves are being transmitted. In a case where the receipt signal level is the target level or higher, the control unit 230 terminates the adjustment process.

As described above, according to the ultrasonic probe 300 of the present embodiment, mounting the attachment 320 for an ultrasonic probe onto the ultrasonic probe body 310 makes it possible to protect the ultrasonic probe body 310 (in particular, the ultrasonic transducer device 100), and thus it is possible to prevent damage to the ultrasonic probe body 310 during carrying, such as with, for example, a portable diagnostic apparatus. It is also possible to carry out the adjustment process for the ultrasonic probe body 310 using the protective member 322 as the ultrasonic phantom when the attachment 320 for an ultrasonic probe has been mounted, and thus the need to have already prepared a separate ultrasonic phantom for the adjustment process can be obviated and the adjustment process can be readily carried out with a simple configuration. The adjustment process further makes it possible to reduce the variance in the ultrasonic wave intensity between the ultrasonic elements and also, in a case where the polarization of the piezoelectric body films PE has been considerably reduced, makes it possible to reset the polarization, and thus the performance of the ultrasonic probe can be maintained over a long period. As a result, in a case of use in, for example, a portable ultrasonic diagnostic apparatus, it becomes possible inter alia to implement a diagnostic apparatus that is highly precise, highly durable, and suitable for portable use.

5. Electronic Device and Ultrasonic Diagnostic Apparatus

Figure 13:
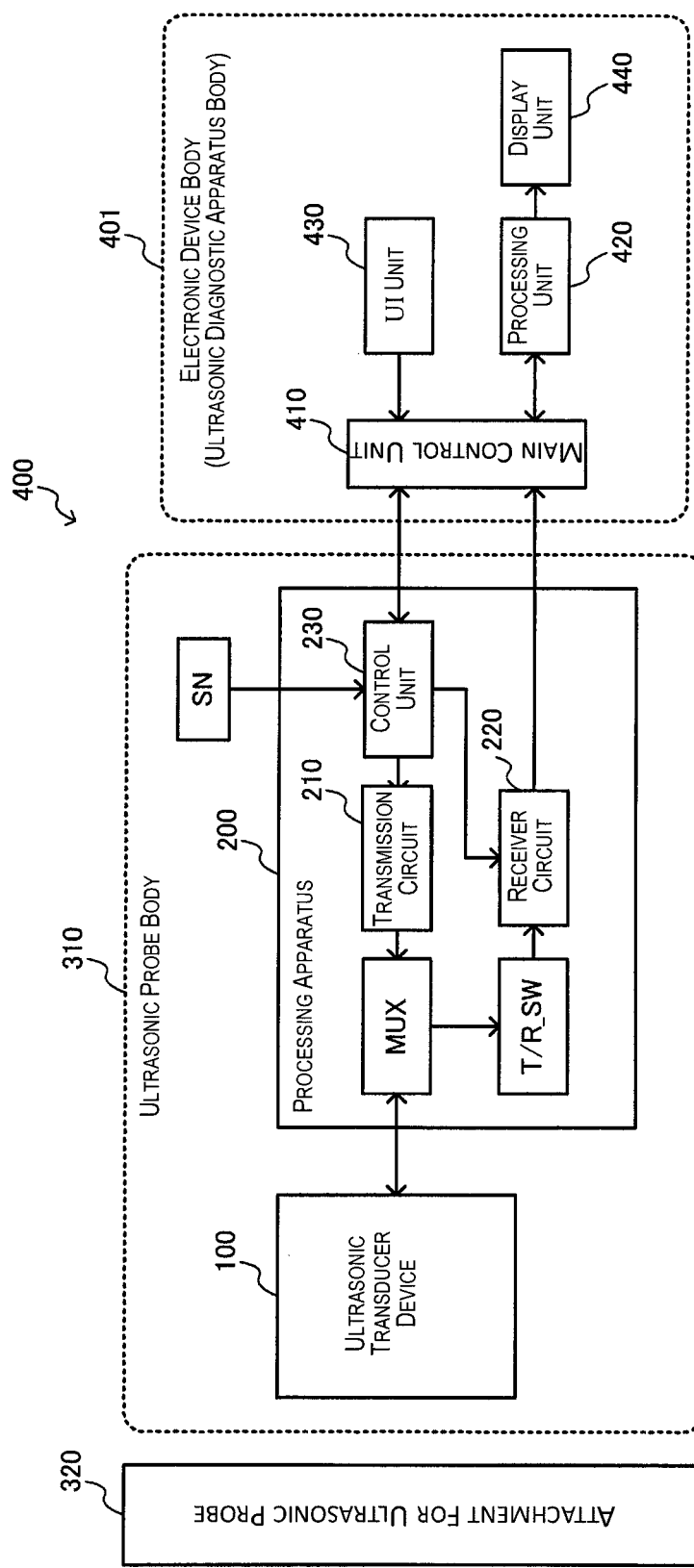
FIG. 13 is an example of a basic configuration for an ultrasonic probe and an electronic device (an ultrasonic diagnostic apparatus)

FIG. 13 is an example of a basic configuration for the ultrasonic probe 300 and an electronic device (an ultrasonic diagnostic apparatus) 400 of the present embodiment. The ultrasonic probe 300 includes the ultrasonic probe body 310 and the attachment 320 for an ultrasonic probe. The ultrasonic probe body 310 includes the ultrasonic transducer device 100 and the processing apparatus 200. The electronic device (ultrasonic diagnostic apparatus) 400 includes the ultrasonic probe 300 and the electronic device body (ultrasonic diagnostic apparatus body) 401. The electronic device body (ultrasonic diagnostic apparatus body) 401 includes the main control unit 410, the processing unit 420, a user interface (UI) unit 430, and the display unit 440.

The main control unit 410 controls the transmission and receipt of ultrasonic waves, in relation to the ultrasonic probe body 310, and controls image process of detection data and the like, in relation to the processing unit 420. The processing unit 420 receives detection data coming from the receiver circuit 220, and carries out necessary image processing, generates image data for display, and the like. The UI unit 430 outputs a necessary order (command) to the main control unit 410 on the basis of an operation carried out by the user (for example, a touch panel operation or the like). The display unit 440 is, for example, a liquid crystal display or the like, and displays the image data for display coming from the processing unit 420. Some of the control carried out by the main control unit 410 may be carried out by the control unit 230 of the processing apparatus 200, or some of the control carried out by the control unit 230 may be carried out by the main control unit 410.

Figure 14A:
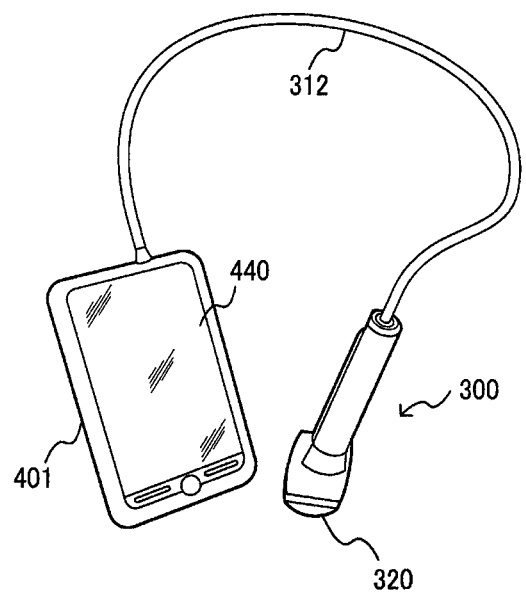
FIGS. 14A and 14B are examples of configurations for an ultrasonic diagnostic apparatus.
Figure 14B:
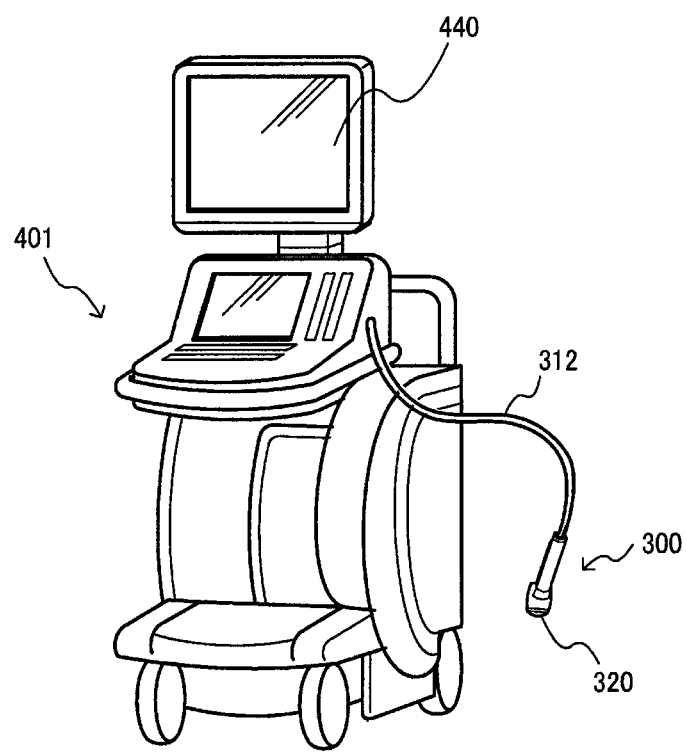

FIGS. 14A and 14B illustrate examples of configurations for the ultrasonic diagnostic apparatus 400 of the present embodiment. FIG. 14A illustrates a portable version of the ultrasonic diagnostic apparatus 400, and FIG. 14B illustrates a floor-standing version of the ultrasonic diagnostic apparatus 400; both illustrate a state where the attachment 320 for an ultrasonic probe has been mounted.

Both the portable version and the floor-standing version of the ultrasonic diagnostic apparatus 400 include the ultrasonic probe 300, the cable 312, and the ultrasonic diagnostic device body (electronic device body) 401. The ultrasonic probe 300 includes the ultrasonic probe body 310 and the attachment 320 for an ultrasonic probe, and the ultrasonic probe body 310 is connected to the ultrasonic diagnostic apparatus body (electronic device body) 401 by the cable 312. The ultrasonic diagnostic apparatus body (electronic device body) 401 includes the display unit 440 for displaying the image data for display.

Though the present embodiment has been described in greater detail above, it shall be readily understood by a person skilled in the art that there are numerous possible modifications which do not substantially depart from the novel features and effects of the present invention. As such, the modification examples of such description are understood to all also be included in the scope of the present invention. For example, a phrase (ultrasonic diagnostic apparatus, ultrasonic diagnostic apparatus body) mentioned at least once along with a different phrase (electronic device, electronic device body) of either a broader meaning or identical meaning in the description or drawings could also be replaced with that different phrase anywhere in the description or drawings. The configurations and operations of the attachment for an ultrasonic probe, the ultrasonic probe, the electronic device, and the ultrasonic diagnostic apparatus are also not limited to those described in the present embodiment, and a variety of modifications can be implemented.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An attachment for an ultrasonic probe adapted to be mounted onto an ultrasonic probe body of the ultrasonic probe, the attachment for an ultrasonic probe comprising:
    a cover member configured to cover an ultrasonic wave emission surface of a head section of the ultrasonic probe body when the attachment is mounted onto the ultrasonic probe body;
    a protective member disposed on an inner surface of the cover member facing the ultrasonic wave emission surface and configured to be in contact with the ultrasonic wave emission surface when the attachment is mounted onto the ultrasonic probe body; and
    a reflector that is arranged in the protective member such that the reflector is provided between the cover member and the ultrasonic wave emission source when the attachment is mounted onto the ultrasonic probe body, the reflector having an acoustic impedance greater than an acoustic impedance of the protective member,
    the inner surface of the cover member and the reflector being configured to reflect ultrasonic waves emitted from the ultrasonic wave emission surface to the ultrasonic wave emission surface such that the ultrasonic probe carries out an adjustment process to the ultrasonic probe body by using the ultrasonic waves that the inner surface of the cover member and the reflector have been reflected.

2. The attachment for the ultrasonic probe according to claim 1, wherein
    the protective member is formed of a shape and material configured to be in intimate contact with the ultrasonic wave emission surface when the attachment is mounted onto the ultrasonic probe body.

3. The attachment for the ultrasonic probe according to claim 2, wherein
    the protective member has a surface that is configured to face the ultrasonic wave emission surface and has a convex shape before the attachment is mounted onto the ultrasonic probe body.

4. The attachment for the ultrasonic probe according to claim 2, wherein
    the protective member has a surface that is configured to face the ultrasonic wave emission surface and has an inclined shape before the attachment is mounted onto the ultrasonic probe body.

5. The attachment for the ultrasonic probe according to claim 1, wherein
    the protective member is formed of a gel material.

6. An ultrasonic probe comprising:
    the attachment for the ultrasonic probe according to claim 1; and
    the ultrasonic probe body.

7. The ultrasonic probe according to claim 6, further comprising
    a fitting section configured to fit the ultrasonic probe body to the cover member in a state where the ultrasonic wave emission surface and the protective member are in intimate contact.

8. The ultrasonic probe according to claim 7, wherein
    the ultrasonic wave emission surface of the ultrasonic probe body and the protective member of the attachment are in intimate contact when the attachment is mounted onto the ultrasonic probe body.

9. An ultrasonic probe comprising:
    a head section including an ultrasonic transducer device, the head section having an ultrasonic wave emission surface; and
    a processing apparatus configured to carry out transmission process and receipt process for the ultrasonic transducer device, the processing apparatus being further configured to carry out an adjustment process to the ultrasonic transducer device by using ultrasonic waves that have been emitted from the ultrasonic wave emission surface and have been reflected to the ultrasonic wave emission surface by an inner surface of a cover member and a reflector when the head section is mounted onto an attachment, the attachment including the cover member, a protective member, and the reflector which is arranged in the protective member, the reflector having an acoustic impedance greater than an acoustic impedance of the protective member, the protective member being disposed on the inner surface of the cover member and having a surface facing the ultrasonic wave emission surface and in contact with the ultrasonic wave emission surface.

10. The ultrasonic probe according to claim 9, wherein the processing apparatus is configured to carry out the adjustment process using as an ultrasonic phantom the protective member as well as the cover member of the attachment when the attachment is mounted onto the ultrasonic probe, the cover member covering the ultrasonic wave emission surface.

11. The ultrasonic probe according to claim 9, further comprising
a detection unit including at least one of a sensor and a switch, and configured to detect mounting of the attachment onto the ultrasonic probe, wherein
the processing apparatus is configured to carry out the adjustment process on a condition that the mounting is detected by the detection unit.

12. The ultrasonic probe according to claim 11, wherein the processing apparatus is configured to carry out a process for instructing that the mounting be done when the mounting is not detected by the detection unit.

13. The ultrasonic probe according to claim 11, wherein the processing apparatus is configured to carry out a process for instructing that the mounting be done when the mounting is not detected by the detection unit after a measurement process.

14. An ultrasonic diagnostic apparatus comprising;
the ultrasonic probe according to claim 6;
a main controller configured to control the ultrasonic probe body to transmit and receive ultrasonic waves; and
an image processor configured to generate image data for display based on the ultrasonic waves received by the ultrasonic probe body.

15. The ultrasonic diagnostic apparatus according to claim 14, further comprising
a display unit configured to display image data for display.

16. The attachment for the ultrasonic probe according to claim 1, wherein
the reflector is wire-shaped or cylinder-shaped.

17. The attachment for the ultrasonic probe according to claim 1, wherein
the cover member has an acoustic impedance greater than the acoustic impedance of the protective member.

18. The attachment for the ultrasonic probe according to claim 1, wherein
the acoustic impedance of the reflector and the acoustic impedance of the cover member are closer to an acoustic impedance of a bone than the acoustic impedance of the protective member.

* * * * *